United States Patent [19]

Wong et al.

[11] Patent Number: 4,892,710
[45] Date of Patent: Jan. 9, 1990

[54] CARTRIDGE ASSEMBLY WITH MULTI-PURPOSE CLOSURE TUBING

[75] Inventors: Raphael C. Wong; That T. Ngo, both of Irvine, Calif.

[73] Assignee: Bioprobe International, Inc., Tustin, Calif.

[21] Appl. No.: 70,764

[22] Filed: Jul. 7, 1987

[51] Int. Cl.$^4$ ................................................. B01L 3/00
[52] U.S. Cl. ..................................... 422/102; 55/387;
73/864.51; 73/864.73; 73/864.74; 210/282;
210/416.1; 222/527; 222/530; 222/538;
422/103; 436/178; 604/326; 604/403; 604/414
[58] Field of Search .............................. 422/102, 103;
73/864.51, 864.73, 864.74; 604/326, 403, 414;
210/282, 416.1; 222/527, 530, 538; 55/387;
436/178

[56] References Cited

U.S. PATENT DOCUMENTS

| | | | |
|---|---|---|---|
| 1,433,075 | 10/1922 | Gottlieb | 422/100 X |
| 3,106,845 | 10/1963 | Dimmick | 422/100 X |
| 3,572,552 | 3/1971 | Guinn | 422/99 X |
| 3,825,410 | 7/1974 | Bagshawe | 422/102 X |
| 4,256,461 | 3/1981 | Wallace et al. | 422/99 X |
| 4,272,478 | 6/1981 | Vihko | 422/102 X |

Primary Examiner—Barry S. Richman
Assistant Examiner—Jill Johnston
Attorney, Agent, or Firm—Nilsson, Robbins, Dalgarn, Berliner, Carson & Wurst

[57] ABSTRACT

A cartridge assembly useful as a sampling or test device includes a cartridge and a closure tubing adapted to close either or both ends of the cartridge and to serve as a conduit for liquids eluted from the cartridge.

9 Claims, 1 Drawing Sheet

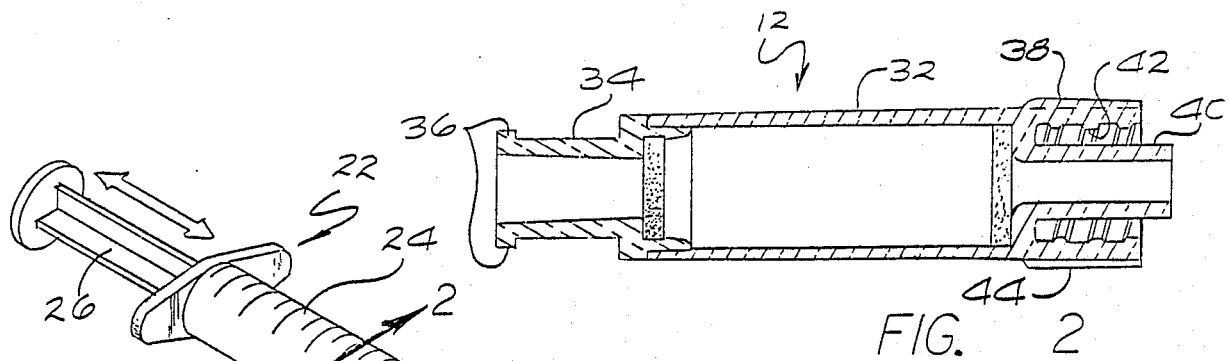
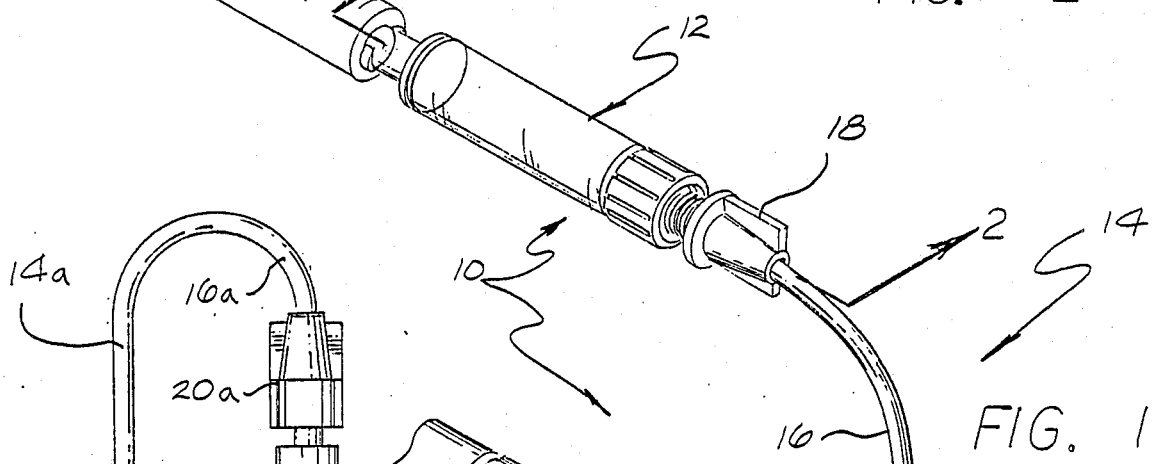
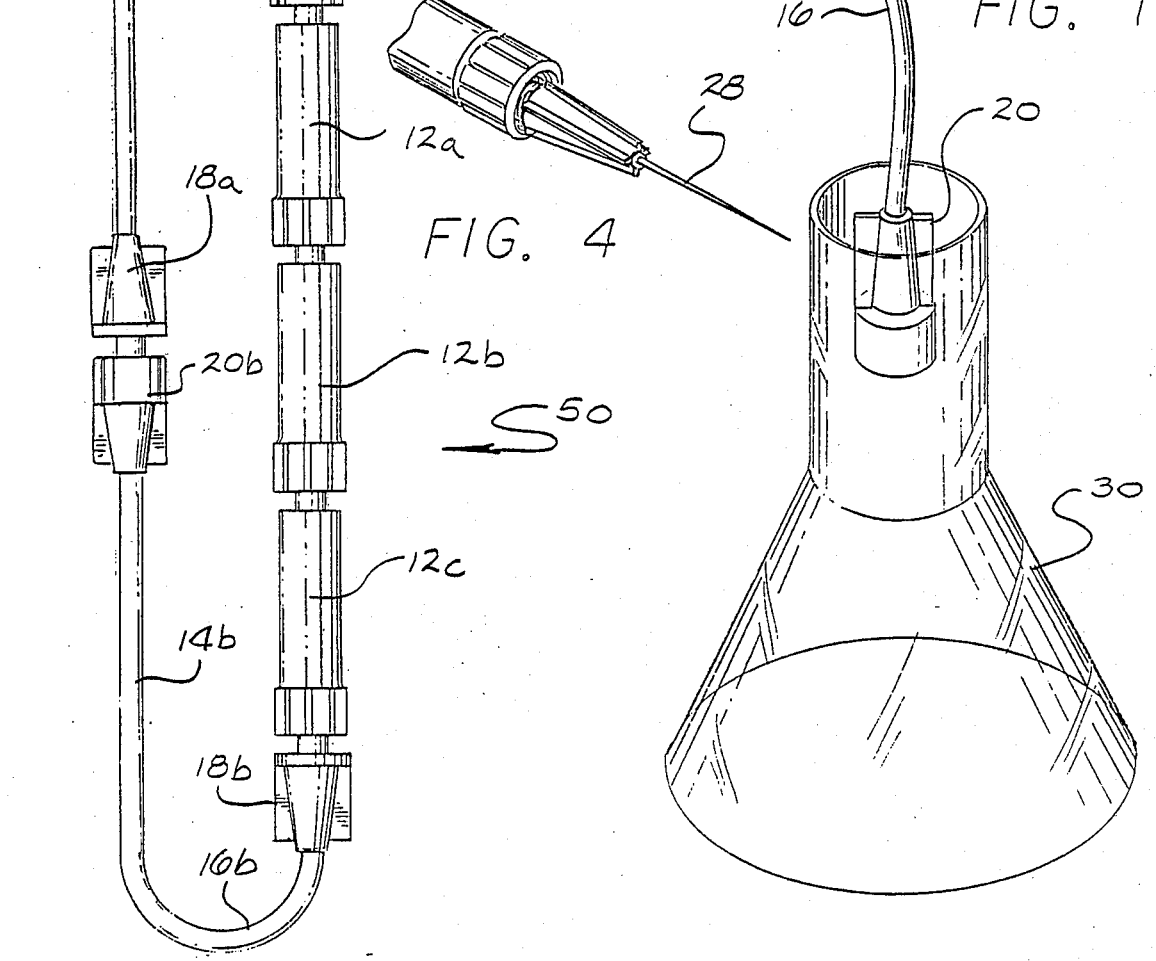

CARTRIDGE ASSEMBLY WITH MULTI-PURPOSE CLOSURE TUBING

BACKGROUND OF THE INVENTION

This invention relates to a cartridge useful as a sampling or test device. In one of its more particular aspects, this invention relates to a cartridge having a multi-purpose closure tubing.

Devices for sampling materials to be analyzed and for analyzing various materials, particularly materials of a biological character are well-known. Most such devices, however, are cumbersome and lack the flexibility that is desirable in sampling and analyzing various biological materials. In addition, conventional analysis frequently require passing an impure mixture containing the biological component to be detected through a suitable column to selectively adsorb the desired component from the mixture. The desired component is then later eluted from the column in a purified form for analysis or whatever other purpose the component is desired. Co-pending application Ser. No. 923,053, filed Oct. 27, 1986 and assigned to the same assignee as the present invention describes a process for the purification of monoclonal antibodies utilizing an immobilized protein A adsorbent and various buffer solutions. In this process conventional columns are used to contain the adsorbent.

With respect to particular devices for use in various biological processes, U.S. Pat. No. 4,212,948 describes the use of centrifugation tubes containing a liquid cushioning agent.

U.S. Pat. No. 4,409,105 describes a column containing dried gamma globulin affixed to a solid carrier.

U.S. Pat. No. 4,476,093 describes a kit containing a water insoluble anti-human alpha$_2$-macroglobulin antibody and a gel of allyl dextran cross linked-with N,N$^1$-methylenebisacrylamide or a gel of polyvinyl alcohol having many hydrophilic hydroxyl groups equilibrated with a pH 7.0–7.4 buffer solution and endotoxin marker solution and a buffer solution.

U.S. Pat. No. 4,543,328 describes a process and device for detecting pathogens in which a biocompatible adsorbent adsorbs the pathogen from a blood sample, with the pathogen being thereafter detected by conventional means.

U.S. Pat. No. 4,469,630 describes a chromatographic separation of monoclonal antibody type IgG from mouse ascites fluid. A particulate silica gel of specified particle size and pore size to which polyethylenimine is bound is utilized in the separation.

U.S. Pat. No. 4,490,290 describes a process for recovering immunoglobulins from natural sources such as milk or blood serum utilizing an insoluble carrier having low affinity monoclonal antibodies bound thereto.

It would be desirable to provide a convenient to use device which is portable, which can be used for sampling purposes, or which can be used to purify or test for various materials, especially materials of biological interest.

Accordingly, it is an object of the present invention to provide an improved sampling and purification device.

It is another object of the present invention to provide such a device which can function both as a container for transporting samples and as a sample purification column.

Another object of the present invention is to provide such a device which can be used with varying volumes of test materials.

Another object of the present invention is to provide such a device, the use of which is characterized by speed and convenience.

Other objects and advantages of the invention will become apparent from the following detailed disclosure.

SUMMARY OF THE INVENTION

The present invention provides a cartridge assembly including a cartridge and a closure tubing fitted with a male end adapted to close one end of the cartridge and a female end adapted to close the other end of the cartridge. Luer locks are utilized as closure means to insure watertight closure.

BRIEF DESCRIPTION OF THE DRAWINGS

FIG. 1 is a perspective view showing the cartridge assembly of the present invention in use.

FIG. 2 is a cross-sectional view of the cartridge of the present invention.

FIG. 3 is a side elevation of three cartridges in tandem.

FIG. 4 is a partial perspective view of a cartridge fitted with a syringe.

DESCRIPTION OF THE PREFERRED EMBODIMENTS

Referring to FIG. 1 of the drawing, the numeral 10 represents a cartridge assembly according to the present invention. Cartridge assembly 10 consists of cartridge 12 and closure 14. Cartridge 12 will be described more particularly with regard to FIG. 2. Closure 14 consists of closure tubing 16 having a male closure 18 at one end thereof and a female closure 20 at the other end. Also shown in FIG. 1 is a syringe 22 which consists of a body 24 and a plunger 26.

FIG. 2 shows the cartridge 12 in greater detail. Throughout the description of the drawings, the same or similar numerals will be used to describe similar parts. As shown in FIG. 2, cartridge 12, which may, for example have a volume of 0.5 ml., 1 ml. or 5 ml., contains a body 32 having a male end 34 fitted with lugs 36 and a female end 38 having at one cartridge an inner tube 40, threads 42 and ribs 44. When lugs 36 are mated with threads 42 of another cartridge, as will be described below, there is formed a luer lock which insures a watertight closure.

FIG. 3 shows a multiplicity of cartridges used in tandem. The purpose of such arrangement is to increase the volume which can be sampled in the cartridges or to increase the length of a column used for purifying a particular substance. Extended column 50 consists of 3 cartridges 12a, 12b and 12c connected in tandem, the lugs 36 of the male end of one cartridge being threadedly engaged with the threads 42 of the female end of another cartridge, forming a luer lock. As shown in FIG. 3, cartridge 12a is thus connected to cartridge 12b which in turn is connected to cartridge 12c. The male end of cartridge 12A is closed by means of the female closure 20a while the female end of cartridge 12c is closed by means of male closure 18b. Since a single closure 14 is of insufficient length to close the tandem assembly of cartridges 12a, 12b and 12c, two closures 14a and 14b connected by means of male closure 18a of closure 14a and female closure 20b of closure 14b. The combined length of closure tubings 16a and 16b is adequate to conveniently close the tandem assembly of cartridges 12a, 12b and 12c. Alternatively, a single closure having a longer tubing could be used.

In sampling, a single cartridge 12 is filled with the material to be sampled, for example, by means of a syringe as shown in FIG. 1. After disconnecting the syringe from the cartridge the sample is maintained secure and uncontaminated by means of closure 14 with the female closure 20 securely closing male end 34 of cartridge 12 by means of lugs 36 and threads within female closure 20 (not shown). Female end 38 of cartridge 12 is similarly closed by male closure 18 as shown in FIG. 1, the threads 42 inside female end 38 of cartridge 12 engaging the external threads of male closure 18 as shown in FIG. 1. Both ends of cartridge 12 are thus closed by luer locks.

For purification of a particular material, a cartridge 12 is filled with a suitable adsorbent such as an immobilized protein A.

Many such suitable adsorbents are commercially available. A purified protein A coupled to cross-linked agarose beads by chemically stable amide bonds can be obtained from Bio-Rad Laboratories, Richmond, Calif. as Affi-Gel ® Protein A. Protein A-Agarose is also available from Zymed Laboratories, Burlingame, Calif. This product is described as a pure protein A coupled to CNBr-activated Sepharose ® 4B. A similar product, Protein A Sepharose ® CL-4B is also available from Pharmacia Fine Chemicals, Uppsala, Sweden. Protein A-Ultrogel ® is available from Reactifs IBF, France. It is described as a biospecific affinity chromatography adsorbent able to interact with different immunoglobulins G from different mammals and is prepared by immobilizing electrophoretically pure protein A to a glutaraldehyde-activated gel. Protein A covalently coupled to cross-linked beaded agarose is also available from Pierce Chemical Co.

An immobilized protein A can also be provided using the techniques disclosed in U.S. Pat. No. 4,582,875, assigned to the same assignee as the present invention, the disclosure of which is hereby incorporated by reference. This patent generally teaches the activation of hydroxyl group-containing polymeric carriers using 2-fluoro-1-methylpyridinium toluene-4-sulfonate (FMP). Such activated polymers are commercially available from BioProbe International, Inc., Tustin, Calif. Avid-Gel ™ FMP-activated hydrophilic gel is an FMP-activated polymer of N-acryloyl-2-amino-2-hydroxymethyl-1, 3-propanediol (Trisacryl GF 2000, Reactifs 2000, France). Avid-Gel F ™ FMP-activated hydrophilic gel is an FMP-activated hydrophilic polyvinyl alcohol composed exclusively of C, H and O atoms (Fractogel TSK, E. Merck, Darmstadt, Germany). Both can be used to provide an immobilized protein A.

As shown in FIG. 1, in use the female closure 20 is uncapped from the male end 34 of cartridge 12 and placed in a container such as flask 30. Closure 14 including male closure 18, closure tubing 16 and female closure 20 thus serves as a conduit for conducting liquid from the cartridge 12 into flask 30. After buffering the adsorbent contained within cartridge 12 and washing by means of a syringe, as shown in FIG. 1, the sample to be purified is then passed through cartridge 12 and the unadsorbed material passes through closure 14 into flask 30. After rinsing the column comprised of cartridge 12 and the adsorbent contained within the cartridge with a suitable buffer, the eluate in flask 30 is discarded and the female closure 20 is placed into a collection container which may be similar to flask 30. Using the syringe as before, suitable buffer is passed through the cartridge to elute the desired material from the adsorbent and the eluate is collected in the collection container. The eluate is the purified component which is eluted from the adsorbent in cartridge 12. Conversely, the sample can be purified by passing it through the cartridge to remove unwanted contaminants by adsorption of the contaminants to the adsorbent. The desired materials are not adsorbed and thus pass through closure 14 into flask 30. For example, in a column containing immobilized protein A, if a mixture of the Fab and Fc antibody chains is applied to the column, the Fc chain is adsorbed upon the column while the Fab chain passes through the column and can be recovered in the flask.

Thus it can be seen that male and female closures connected by a tubing serves not only as a convenient, flexible closure for the cartridge, but also as a conduit for liquids eluted from the cartridge. Use of the cartridge assembly of the present invention facilitates and simplifies manipulations and speeds up the purification process. For instance, using a syringe luer locked to the cartridge of the present invention decreases process time from several hours to about thirty minutes.

The foregoing description of the invention has been directed to particular preferred embodiments for purposes of explanation and illustration. It will be apparent, however, to those skilled in the art that many modifications and changes in the particular methods and materials may be made without departure from the scope and spirit of the invention. For example, a number of cartridges greater or lesser than the numbers shown in the drawings can be utilized to provide columns of varying lengths. Also, the cartridge may be longer or shorter in length, narrower or wider in diameter to suit particular uses. Further, as pointed out above, the length of the closure tubing may be varied. In addition, other processes than those specifically mentioned herein may be conducted utilizing the cartridge assembly of the present invention. It is applicant's intention in the following claims to cover all such equivalents, modifications and changes that fall within the true spirit and scope of the invention.

What is claimed is:

1. A cartridge assembly which comprises:
   at least one cartridge means for sampling, testing or purifying materials having a male end and a female end; and
   a closure tubing having a female end adapted to close the male end of said cartridge means and a male end adapted to close the female end of said cartridge means.

2. A cartridge assembly according to claim 1 wherein said male end of said at least one cartridge means and said closure tubing comprises thread means and said female end of said at least one cartridge means and said closure tubing adapted to close said male end comprises reciprocating thread means.

3. A cartridge assembly according to claim 1 wherein said male end of said at least one cartridge means and said closure tubing comprises lug means and said female end of said at least one cartridge means and said closure tubing adapted to close said male end comprises reciprocating thread means.

4. A cartridge assembly according to claim 1 wherein said cartridge means contains a solid adsorbent material.

5. A cartridge assembly according to claim 1 wherein said at least one cartridge means comprises a plurality of cartridges in tandem connection whereby the male end of one cartridge is connected to the female end of a next cartridge in tandem connection.

6. A cartridge assembly according to claim 5 wherein the male end of at least one of said plurality of cartridges comprises lug or thread means and the female end of a next cartridge in tandem connection comprises reciprocating thread means.

7. A cartridge assembly according to claim 5 wherein the male end of a first cartridge of said plurality of cartridges in the tandem connection is closed by the female end of said closure tubing and the female end of a last cartridge in the tandem connection is closed by the male end of the closure tubing.

8. A cartridge assembly according to claim 5 further comprising at least one additional closure tubing, the female end of one of said closure tubings being connected to the male end of another of said closure tubings.

9. A cartridge assembly comprising:
cartridge means having a male end and a female end; and
a closure tubing having a female end adapted to close the male end of said cartridge means, a male end adapted to close the female end of said cartridge means and a tubing connecting said male and female ends, the cartridge assembly functioning as a closed container when the male and female ends of said cartridge means are closed by means of said closure tubing and functioning as a conduit for a liquid introduced into said container when an end of said closure tubing is disconnected from a reciprocating end of said cartridge means.

* * * * *